US009011905B2

(12) United States Patent
Najarian et al.

(10) Patent No.: US 9,011,905 B2
(45) Date of Patent: *Apr. 21, 2015

(54) LOW DOSE TOPIRAMATE/PHENTERMINE COMPOSITION AND METHODS OF USE THEREOF

(71) Applicant: Vivus, Inc., Mountain View, CA (US)

(72) Inventors: Thomas Najarian, Los Osos, CA (US); Peter Y. Tam, Redwood City, CA (US); Leland F. Wilson, Menlo Park, CA (US)

(73) Assignee: Vivus, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/495,246

(22) Filed: Sep. 24, 2014

(65) Prior Publication Data

US 2015/0010625 A1 Jan. 8, 2015

Related U.S. Application Data

(63) Continuation of application No. 14/048,576, filed on Oct. 8, 2013, now Pat. No. 8,895,058, which is a continuation of application No. 12/481,540, filed on Jun. 9, 2009, now Pat. No. 8,580,298, which is a continuation-in-part of application No. 12/135,953, filed on Jun. 9, 2009, now abandoned.

(51) Int. Cl.

| | |
|---|---|
| ***A61K 9/48*** | (2006.01) |
| ***A61K 31/7048*** | (2006.01) |
| ***A61K 31/137*** | (2006.01) |
| ***A61K 31/35*** | (2006.01) |
| ***A61K 31/357*** | (2006.01) |
| ***A61K 9/28*** | (2006.01) |

(52) U.S. Cl.

CPC ........... *A61K 31/7048* (2013.01); *A61K 31/137* (2013.01); *A61K 31/35* (2013.01); *A61K 31/357* (2013.01); *A61K 9/28* (2013.01)

(58) Field of Classification Search

None

See application file for complete search history.

(56) References Cited

U.S. PATENT DOCUMENTS

| | | | | |
|---|---|---|---|---|
| 4,513,006 | A | 4/1985 | Maryanoff et al. | |
| 4,792,569 | A | 12/1988 | Maryanoff et al. | |
| 4,895,845 | A | 1/1990 | Seed | |
| 5,242,391 | A | 9/1993 | Place et al. | |
| 5,242,942 | A | 9/1993 | Costanzo et al. | |
| 5,266,591 | A | 11/1993 | Wierzbicki et al. | |
| 5,273,993 | A | 12/1993 | Lo et al. | |
| 5,384,327 | A | 1/1995 | Costanzo et al. | |
| 5,474,535 | A | 12/1995 | Place et al. | |
| 5,498,629 | A | 3/1996 | Costenzo et al. | |
| 5,527,788 | A | 6/1996 | Svec et al. | |
| 5,543,405 | A | 8/1996 | Keown et al. | |
| 5,753,693 | A | 5/1998 | Shank | |
| 5,753,694 | A | 5/1998 | Shank | |
| 5,773,020 | A | 6/1998 | Place et al. | |
| 5,795,895 | A | 8/1998 | Anchors | |
| 5,885,616 | A | 3/1999 | Hsiao et al. | |
| 5,900,418 | A | 5/1999 | Viner | |
| 6,071,537 | A | 6/2000 | Shank | |
| 6,201,010 | B1 | 3/2001 | Cottrell | |
| 6,319,903 | B1 | 11/2001 | Carrazana et al. | |
| 6,323,236 | B2 | 11/2001 | McElroy | |
| 6,362,220 | B1 | 3/2002 | Cottrell | |
| 6,620,819 | B2 | 9/2003 | Marcotte | |
| 6,627,653 | B2 | 9/2003 | Plata-Salaman et al. | |
| 6,686,337 | B2 | 2/2004 | Connor | |
| 6,908,902 | B2 | 6/2005 | Plata-Salaman et al. | |
| 7,056,890 | B2 * | 6/2006 | Najarian | 514/23 |
| 7,109,174 | B2 | 9/2006 | Plata-Salaman et al. | |
| 7,109,198 | B2 | 9/2006 | Gadde et al. | |
| 7,351,695 | B2 | 4/2008 | Almarssoo et al. | |
| 7,429,580 | B2 | 9/2008 | Gadde et al. | |
| 7,553,818 | B2 | 6/2009 | Najarian | |
| 7,659,256 | B2 | 2/2010 | Najarian | |
| 7,674,776 | B2 * | 3/2010 | Najarian | 514/23 |
| 8,580,298 | B2 * | 11/2013 | Najaraian et al. | 424/451 |
| 8,580,299 | B2 * | 11/2013 | Najarian et al. | 424/451 |
| 8,895,057 | B2 | 11/2014 | Najarian et al. | |
| 8,895,058 | B2 | 11/2014 | Najarian et al. | |

(Continued)

FOREIGN PATENT DOCUMENTS

| | | | |
|---|---|---|---|
| CA | 2377330 | A1 | 12/2000 |
| CA | 2686633 | A1 | 12/2000 |

(Continued)

OTHER PUBLICATIONS

"An Open Letter (Email) to Lazard." VivusPatent Wordpress. Sep. 6, 2013. Web. Sep. 13, 2013. http://vivuspatent.wordpress.com/2013/09/06/an-open-letter-email-to-lazard/.

FDC Reports, Inc. "Appetite Suppression Drugs Excluded by 81% of Employers—PBMI Survey." The Green Sheet, 48.19:3 (1999).

"Cowen's Response is Inadequate & Incomplete." VivusPatent Wordpress. Jul. 21, 2012. Web. Sep. 13, 2013. http://vivuspatent.wordpress.com/2012/07/21/cowens-response-is-inadequate-incomplete/.

"Daniel B. Ravicher's Response to Qsymia Patent Report: Why Reasonable People Hate Ethically-Challenged Lawyers." VivusPatent Wordpress. Aug. 4, 2012. Web. Sep. 13, 2013. http://vivuspatent.wordpress.com/2012/08/04/daniel-b-ravichers-response-to-qsymia-patent-report-why-reasonable-people-hate-ethically-challenged-lawyers/.

(Continued)

*Primary Examiner* — Hasan Ahmed

(74) *Attorney, Agent, or Firm* — Cooley LLP; Ivor R. Elrifi; Matthew Pavao

(57) ABSTRACT

A method for effecting weight loss by administering a combination of topiramate and phentermine is provided. The phentermine is generally administered in immediate release form, in a daily dose in the range of 2 mg to 8 mg, in combination with a daily dose of topiramate selected to prevent the loss of effectiveness of phentermine alone. Methods for treating obesity, conditions associated with obesity, and other indications are also provided, as are compositions and dosage forms containing low doses of phentermine and topiramate, e.g., 3.75 mg phentermine and 23 mg topiramate.

38 Claims, 2 Drawing Sheets

(56) References Cited

U.S. PATENT DOCUMENTS

| | | | |
|---|---|---|---|
| 2003/0072802 | A1 | 4/2003 | Cutler |
| 2004/0002462 | A1 | 1/2004 | Najarian |
| 2004/0122033 | A1 | 6/2004 | Nargund et al. |
| 2005/0032773 | A1 | 2/2005 | Piot-Grosjean et al. |
| 2005/0065190 | A1 | 3/2005 | Hinz |
| 2006/0058293 | A1 | 3/2006 | Weber et al. |
| 2006/0234950 | A1 | 10/2006 | Najarian |
| 2007/0129283 | A1 | 6/2007 | McKinney et al. |
| 2008/0085306 | A1 | 4/2008 | Nangia et al. |
| 2008/0103179 | A1 | 5/2008 | Tam et al. |
| 2008/0118557 | A1 | 5/2008 | Liang et al. |
| 2008/0255093 | A1 | 10/2008 | Tam et al. |
| 2009/0304785 | A1 | 12/2009 | Najarian et al. |
| 2009/0304789 | A1 | 12/2009 | Najarian et al. |
| 2010/0105765 | A1 | 4/2010 | Najarian |
| 2010/0215739 | A1 | 8/2010 | Najarian et al. |
| 2011/0262535 | A1 | 10/2011 | Najarian et al. |

FOREIGN PATENT DOCUMENTS

| | | | |
|---|---|---|---|
| CA | 2727313 | A1 | 12/2009 |
| WO | WO 00/50020 | A2 | 8/2000 |
| WO | WO 00/76493 | A1 | 12/2000 |
| WO | WO 2005/063206 | A1 | 7/2005 |
| WO | WO 2006/063078 | A2 | 6/2006 |
| WO | WO-2006/071740 | A2 | 7/2006 |
| WO | WO 2006/088748 | A2 | 8/2006 |
| WO | WO 2006/124506 | A2 | 11/2006 |
| WO | WO 2007/084290 | A2 | 7/2007 |
| WO | WO 2008/050020 | A1 | 5/2008 |
| WO | WO 2008/060963 | A2 | 5/2008 |
| WO | WO 2008/153632 | A2 | 12/2008 |
| WO | WO 2008/156550 | A2 | 12/2008 |
| WO | WO 2009/061436 | A1 | 5/2009 |
| WO | WO 2011/085256 | A2 | 7/2011 |

OTHER PUBLICATIONS

"Drug Therapies: Fastin, Ionamin (Phentermine)." Planet RD, Inc. (1999):3-4. www.obesity.com.

"Email to Mintz Levin re: 2007 Vivus Conference Call <http://vivuspatent.wordpress.com/2013/11/08/email-to-mintz-levin-re-2007-vivus-conference-call/>" VivusPatent World Press. Nov. 8, 2013. Web. Nov. 8, 2013. http://vivuspatent.wordpress.com/2013/11/08/email-to-mintz-levin-re-2007-vivus-conference-call/.

"Fastin (Phentermine HCl) Capsules." U.S. Food and Drug Administration. Drug Labeling Changes. (1997). www.fda.gov/medwatch/safety/1997/oct97.htm.

"Intellectual Property Diligence for Vivus' Obesity Drug Qsymia." VivusPatent Wordpress. Jul. 20, 2012. Web. Sep. 13, 2013. http://vivuspatent.wordpress.com/2012/07/20/intellectual-property-diligence-for-vivus-obesity-drug-qsymia/.

"Ionamin (phentermine resin) Capsules." U.S. Food and Drug Administration. (1998). www.fda.gov/medwatch/safety/1998/feb98.htm.

"McElroy FTO—My Bad." VivusPatent Wordpress. Jul. 22, 2012. Web. Sep. 13, 2013. http://vivuspatent.wordpress.com/2012/07/22/mcelroy-fto-my-bad/.

"Memorandum from Division of Metabolism and Endocrinology Products (DMEP)." Department of Health and Human Services. May 22, 2007.

"Phentermine Hydrochloride." Physicians' Desk Reference. Montvale, NJ: Medical Economics Data Production Company. (1995):2508-2509.

"Phentermine." Physicians' Desk Reference. (1999):1053-1054.

"Sibutramine." The Merck Index, 13 Edition, No. 8559:1522 (2001).

"Two New Issued Qsymia Patents: Where Does Vivus Stand Now.?" VivusPatent Wordpress. Nov. 14, 2013. Web. Nov. 15, 2013. http://vivuspatent.wordpress.com/2013/11/14/two-new-issued-qsymia-patents-where-does-vivus-stand-now/.

"Vivus Qsymia Patents: Appearance of Ongoing and Systematic Inequitable Conduct before the USPTO by Vivus and its Attorneys." VivusPatent Wordpress. Aug. 12, 2013. Web. Sep. 13, 2013. http://vivuspatent.wordpress.com/2013/08/12/159.

"Vivus Qsymia Patents: Intellectual Property House of Cards." VivusPatent Wordpress. Aug. 8, 2013. Web. Sep. 13, 2013. http://vivuspatent.wordpress.com/2013/08/08/vivus-qsymia-patents-intellectual-property-house-of-cards/.

"Wisdom From the Vivus Message Board." VivusPatent Wordpress. Aug. 5, 2012. Web. Sep. 13, 2013. http://vivuspatent.wordpress.com/2012/08/05/wisdom-from-the-vivus-message-board/.

Alger et al. "Effect of Phenylpropanolamine on Energy Expenditure and Weight Loss in Overweight Women", Am. J. Clin., 57:120-126 (1993).

Allen. "Methylcellulose." Handbook of Pharmaceutical Excipients. Web. (Jan. 2000).

Barcena et al. "Diagnosis and Treatment of Sleep Apnea in Heart Disease." Curr. Treat. Opt. Cardiovasc. Med. 9.6:501-509 (2007).

Barry et al. "Presurgical Electroencephalographic Patterns and Outcomes From Anterior Temporal Lobectomy." Arch. Neurol. 49:21-27 (1992).

Barth. "Cannabinoid Receptor Agonists and Antagonists." Exp. Opin. Ther. Patents. 8.3:301-313 (1998).

Bootsma et al. "Topiramate in Clinical Practice: Long-Term Experience in Patients with Refractory Epilepsy Referred to a Tertiary Epilepsy Center." Epilepsy Behavior. 5:380-387 (2004).

Bradley et al. "Bupropion SR with Phentermine for Weight Reduction." Book of Abstracts, American Psychiactric Association Meeting (distributed to meeting attendees). Washington, D.C.(1999). (Abstract Only).

Bray et al. "Current and Potential Drugs for Treatment of Obesity." Endocrine Rev. 20.6:805-875 (1999).

Bray et al. "Pharmacological Treatment of the Overweight Patient." Pharmaco. Rev. 59.2:151-184 (2007).

Bray et al. "Topiramate Produces Dose-Related Weight Loss." 62nd Annual American Diabetes Association Meeting. San Francisco, CA. (2002).

Campbell et al. "Pharmacologic Options for the Treatment of Obesity." Am. J. Health-Syst. Pharm. 58:1301-1308 (2011).

Carek et al. "Current Concepts in the Pharmacological Management of Obesity." Drugs. 6:883-904 (1999).

Citation filed by a third party in European Application No. 09763479.4 dated Nov. 6, 2013.

Citation filed by a third party in European Application No. 09763480.2 dated Nov. 6, 2013.

Communication pursuant to Rule 114(2) EPC issued in European Application No. 070114723 dated Aug. 9, 2013.

Communication pursuant to Rule 114(2) EPC issued in European Application No. 09763479.4 dated Nov. 14, 2013.

Communication pursuant to Rule 114(2) EPC issued in European Application No. 09763480.2 dated Nov. 14, 2013.

Coyne. Letter from Medeva Pharmaeuticals. (1997). www.fds.gov/medwatch/safety/1997/ionami2.htm.

Dahl. "Ethylcellulose." Handbook of Pharmaceutical Excipients. Web. (Jan. 2000).

Després et al. "Effects of Rimonabant on Metabolic Risk Factors in Overweight Patients with Dyslipidemia." New Eng. J. Med. 353:2121-2134 (2005).

European Communication issued in European Application No. 00939884.3 mailed May 25, 2004.

Exhibit 99.1: Conference Call Transcript from Nov. 9, 2007 regarding VVUS—Q3 2007 Vivus Earnings Conference Call. http://yahoo.brand.edgar-online.com/displayfilinginfo.aspx?FilingID=5538387-6827-59035&type=sect&tabindex=2&CompanyID=3684.

Faught et al. "Topiramate Dose-Ranging Trail in Refractory Partial Epilepsy." Epilepsia. 36.S4:33 (1995). (Abstact #D9).

Faught et al. "Topiramate Placebo-Controlled Dose-Ranging Trial in Refractory Partial Epilepsy Using 200-, 400-, and 600-mg Daily Dosages." Neurology. 46:1684-1690 (1996).

FDA: Memorandum from Division of Metabolism and Endocrinology Products (May 22, 2007).

Gadde et al. "A 24-Week Randomized Controlled Trial of VI-0521, a Combination Weight Loss Therapy, in Obese Adults." Obesity. 14.S:A17-A18. (2006) (Abstract #55-OR).

(56) References Cited

OTHER PUBLICATIONS

Gadde et al. "Bupropion SR in Obesity: A Randomized Double-Blind Placebo-Controlled Study." Obesity Res. 7.S1:51F. (1999) (Abstract #0136).
Gadde et al. "Cannabinoid-1 Receptor Antagonist, Rimonabant, for Management of Obesity and Related Risks." Circulation. 114:974-984 (2006).
Gadde et al. "Combination Therapy of Zonisamide and Bupropion for Weight Reduction in Obese Women: A Preliminary, Randomized, Open-Label Study." J. Clin. Psychiatry. 68.8:1226-1229 (2007).
Gadde et al. "Effects of Low-Dose, Controlled-Release, Phentermine Plus Topiramate Combination on Weight and Associated Comorbidities in Overweight and Obese Adults (CONQUER): A Randomised, Placebo-Controlled, Phase 3 Trial." Lancet. 377:1341-1352 (2011).
Garvey et al. "Two-Year Sustained Weight Loss and Metabolic Benefits with Controlled-Release Phentermine/Topiramate in Obese and Overweight Adults (SEQUEL): A Randomized, Placebo-Controlled, Phase 3 Extension Study." Am. J. Clin. Nutr. (2011).
Glauser. "Topiramate." Epilepsia. 40.S5:S71-S80 (1999).
Glazer et al. "Long-Term Pharmacotherapy of Obesity 2000." Arch. Intern. Med. 161.15:1814-1824 (2001).
Goldberg et al. "Lithium Treatment of Bipolar Affective Disorders Under Naturalistic Followup Conditions." Psychopharmacol. Bull. 32.1:47-54 (1996).
Greenway et al. "Bupropion and Zonisamide for the Treatment of Obesity." Obesity. 14.S:A17 (2006). (Abstract #52-OR).
Griffen et al. "The 'phen-pro' Diet Drug Combination is not Associated with Valvular Heart Disease." Arch. Intern. Med. 158.11:1278-1279 (1998).
Hillard et al. "Synthesis and Characterization of Potent and Selective Agonists of the Neuronal Cannibinoid Receptor (CB1)." J. Pharmacol. Exp. 289.3:1427-1433 (1999).
Hobbs. "Vivus' Qnexa Phase 2 Study Results Demonstrate Significant Weight Loss and Reduction in Waist Circumference." Medical News Today. (2006). www.medicalnewstoday.com/articles/54854.php.
Hobbs. "Qnexa: Phentermine-Topriamate Drug Combo Causes Half of Patients to Lose an Average of 25 Pounds." Fatnews.com May 12, 2006. Retrieved Dec. 17, 2012. fatnews.com/index.php/weblog/comments/qnexa- hentermine-topriamate-drug-combo-causes-half-of-patients-to-lose-an-average-of-24-pounds.htm.
Jallon et al. "Bodyweight Gain and Anticonvulsants." Drug Safety. 24.13:969-978 (2011).
Kaplan. "Pharmacological Therapies for Obesity." Gastroenterol. Clin. N. Am. 34:91-104 (2005).
Kibbe. "Povidone." Handbook of Pharmaceutical Excipients. Web. (Jan. 2000).
Kitagawa. "Treatment of Cluster Headache." Prog. Med. Sc. 215. 14(2005):1132-1136. (Japanese Original, No English Translation Available).
Korean Topiramate Study Group. "Low Dose and Slow Titration of Topiramate as Adjunctive Therapy in Refractory Partial Epilepsies: A Multicentre Open Clinical Trial." Seizure. 11:255-260 (2002).
Left. "Vivus (NASDAQ: VVUS): Why FDA Approval is not the Prescription." Citron Research. Jul. 19, 2012. Web. Sep. 13, 2013. <http://www.citronresearch.com/vivus-why-fda-approval-is-not/>.
Makriyannis et al. "Therapeutic Opportunities Through Modulation of the Endocannabinoid System." Neuropharmacol. 48:1068-1071 (2005).
Masand. "Weight Gain Assocaited with Psychotropic Drugs." Exp. Opin. Pharmacotherapy. 1.3:377-389 (2000).
McElroy et al. "Topiramate in the Treatment of Binge Eating Disorder Associated With Obesity: A Randomized Placebo-Controlled Trial." Am. J. Psych. 160.2:255-261 (2003).
Michelucci et al. "The Preclinical and Therapeutic Activity of the Novel Anticonvulsant Topiramate." CNS Drug Rev. 4.2:165-186 (1998).
Murray et al. "Global Mortality, Disability, and the Contribution of Risk Factors: Global Burden of Disease Study." Lancet. 349:1436-1442 (1997).
NIH. "Clinical Guidelines on the Identification, Evaluation, and Treatment of Overweight and Obesity in Adults." NIH Publication No. 98-4083. (Sep. 1998).
Onuma et al. "A Late Phase-II Clinical Study of Topiramate (KW-6485) in Refractory Epilepsy." J. New. Rem. Clin. 56.10:1659-1681 (2007). (Japanese Original and English Abstract).
Partial International Search Report (Invitation to Pay Fees) issued in International Application No. PCT/US2008/005549 mailed Nov. 12, 2008.
Penovich et al. "Weight Loss in Patients Receiving Topiramate for Intractable Epilepsy." Neurology. 44.S2 (1994). (Abstract #309P).
Pi-Sunyer et al. "A Review of Long-Term Studies Evaluating the Efficacy of Weight Loss in Ameliorating Disorders Associated with Obesity." Clin. Ther. 18.6:1006-1035 (1996).
Pi-Sunyer et al. "Effect of Rimonabant, a Cannabinoid-1 Receptor Blocker, on Weight and Cardiometabolic Risk Factors in Overweight or Obese Patients: RIO-North America: A Randomized Controlled Trial." JAMA. 295.7:761-775 (2006).
Potter et al. "Sustained Weight Loss Associated with 12-Month Topiramate Therapy." Epilepsia. 38.S8:97 (1997).
Privitera, "Topiramate: A new antiepileptic drug", Annals of Pharmacotherapy, 31.10:1164-1173 (1997).
Raritan. "Clinical Development of Topiramate of Obesity Extended to Simplify Dosing, Improve Tolerability." Johnson & Johnson Pharmaceutical Research & Development. (2002). www.jnj.com/news/finance/448.htm.
Ravicher. "Report Raising Vivus Qsymia Patent Infringement Concerns was not Competent." Seeking Alpha. Jul. 31, 2013. Web. Sep. 13, 2013. <http://seekingalpha.com/article/765111-report-raising-vivus-qsymia-patent-infringement-concerns-was-not-competent?source=feed>.
Reaven. "Role of Insuline Resistance in Human Disease (Syndrome X): An Expanded Definition." Annu. Rev. Med. 44:121-131 (1993).
Rosenstock et al. "A Randomized, Double-Blind, Placebo-Controlled, Multicenter Study to Assess the Efficacy and Safety of Topiramate Controlled Release in the Treatment of Obese Type 2 Diabetic Patients." Diabetes Care. 30.6:1480-1486 (2007).
Sachdeo et al. "Topiramate: Clinical Profile in Epilepsy." Clin. Pharmacokinet. 34.5:335-346 (1998).
Sachdeo et al. "Topiramate: Double-Blind Trial as Monotherapy." Epilespia. 36.S4:33 (1995). (Abstract #D8).
Shapira, et al., "Treatment of Binge-Eating Disorder with Topiramate: A Clinical Case Series", Journal of Clinical Psychiatry, 61.5:368-372 (2000).
Smith, P. et al., "Weight loss in moderately obese patients with sleep apnea", Ann. Intern. Med. 103.6, pt 1:850-855 (1985) (Abstract only).
Strejan et al. "Suppression of Chronic-Relapsing Experimental Allergic Encephalomyelitis in Strain-12 Guinea Pigs by Administration of Liposome-Associated Myelin Basic Protein." J. Neuroimmunol. 7:27-41 (1984).
Sussman et al. "Anterior Thalamic Stimulation in Medically Intractable Epilepsy. Part II: Preliminary Clinical Results." Epilepsia. 29.5:677 (1988). (Abstract Only).
Sussman et al. "Magnetic Resonance Imaging After Corpus Callosotomy." Neurol. 37:350-354 (1987).
Teva Pharmaceuticals. "ADIPEX-PÒ Prescribing Information." (Jan. 2012).
The Merck Index. Budavari et al., eds. Whitehouse Station, NJ: Merck & Co., Inc. (1996):1151-1152, 2232, 2869, 3167, 3181, 3453, 5895, 7415-7416, and 9931.
The Merck Index. Budavari et al., eds. Whitehouse Station, NJ: Merck & Co., Inc. (1996):187-118, 364, 475, 528-529, 574, 998, 1251-1252, and 1670.
The Merck Index, an Encyclopedia of Chemicals, Drugs, and Biologicals, Twelfth Edition, Published by Merck Research Laboratories (1996).
Third Party Observation filed in European Application No. 09763480.2 dated Nov. 6, 2013.
Tohen et al. "Two-Year Syndromal and Functional Recovery in 219 Cases of First-Episode Major Affective Disorder with Psychotic Features." Am. J. Psychiatry. 157.2:220-228 (2000).
U.S. Appl. No. 60/121,339, filed Feb. 24, 1999.

(56) References Cited

OTHER PUBLICATIONS

U.S. Appl. No. 60/854,756, filed Oct. 27, 2006.
U.S. Appl. No. 61/002,002, filed Nov. 6, 2007.
Vivus, Inc. "Qsymia.RTM Prescribing Information Sheet." (Apr. 2013).
Weintraub et al. "A Double-Blind Clinical Trial in Weight Control." Arch. Intern. Med. 144:1143-1148 (1984).
Wheatley. "Cellulose, Microcrystalline." Handbook of Pharmaceutical Excipients. Web. (Jan. 2000).
Zarate. "Antipsychotic Drug Side Effect Issues in Bipolar Manic Patients." J. Clin. Psychiatry. 61.3S8:52-61 (2000).

* cited by examiner

LOW DOSE TOPIRAMATE/PHENTERMINE COMPOSITION AND METHODS OF USE THEREOF

CROSS-REFERENCE TO RELATED APPLICATIONS

This application is a continuation of U.S. Ser. No. 14/048,576, filed Oct. 8, 2013, which is a continuation of U.S. Ser. No. 12/481,540, filed Jun. 9, 2009, now U.S. Pat. No. 8,580,298, which is a continuation-in-part of U.S. Ser. No. 12/135,953, filed Jun. 9, 2008. The contents of each of these applications are incorporated by reference in their entirety.

BACKGROUND OF THE INVENTION

The prevalence of obesity in both children and adults is on the rise in first world countries, especially in the United States, as well as in many developing countries such as China and India. Many aspects of a person's life are affected by obesity, from physical problems such as knee and ankle joint deterioration, to emotional problems resulting from self-esteem issues and society's attitude towards heavy people. The medical problems caused by obesity can be serious and often life-threatening and include diabetes, shortness of breath and other respiratory problems such as asthma and pulmonary hypertension, gallbladder disease, dyslipidemia (for example, high cholesterol or high levels of triglycerides) and dyslipidemic hypertension, osteoarthritis and other orthopedic problems, reflux esophagitis (heartburn), snoring, sleep apnea, menstrual irregularities, infertility, problems associated with pregnancy, gout, cardiovascular problems such as coronary artery disease and other heart trouble, muscular dystrophy, and metabolic disorders such as hypoalphalipoproteinemia, familial combined hyperlipidemia, and Syndrome X, including insulin-resistant Syndrome X. In addition, obesity has been associated with an increased incidence of certain cancers, notably cancers of the colon, rectum, prostate, breast, uterus, and cervix.

Obesity substantially increases the risk of morbidity from hypertension, dyslipidemia, type II diabetes, coronary heart disease, stroke, gallbladder disease, osteoarthritis and endometrial, breast, prostate, and colon cancers. Higher body weights are also associated with increases in all-cause mortality. Many of these problems are relieved or improved when the afflicted individual undergoes permanent significant weight loss. Weight loss in these individuals can also promote a significant increase in longevity.

Strategies for treating obesity and related disorders have included dietary restriction, increased physical activity, pharmacological approaches, and even surgery, with the choice depending, at least in part, on the degree of weight loss one is attempting to achieve as well as on the severity of obesity exhibited by the subject. For example, treatments such as a low-calorie, low-fat diet and/or regular exercise are often adequate with individuals who are only mildly overweight. The difficulty in maintaining long-term weight loss through diet and behavior modification, however, has led to an increasing interest in other avenues for treatment, particularly pharmacotherapy.

Traditional pharmacological interventions typically induce a weight loss of between five and fifteen kilograms; if the medication is discontinued, renewed weight gain often ensues. Surgical treatments are comparatively successful and are reserved for patients with extreme obesity and/or with serious medical complications.

The above treatments can be enhanced by controlled use of over-the-counter appetite suppressants including caffeine, ephedrine and phenylpropanolamine (Acutrim®, Dexatrim®). Moreover, prescription medications including amphetamine, diethylpropion (Tenuate®), mazindol (Mazanor®, Sanorex®), phentermine (Fastin®, Ionamin®), phenmetrazine (Preludin®), phendimetrazine (Bontrol®, Plegine®, Adipost®, Dital®, Dyrexan®, Melfiat®, Prelu-2®, Rexigen Forte®), benzphetamine (Didrex®) and fluoxetine (Prozac®) are often used in the treatment of seriously overweight and/or obese subjects or patients.

While society has seen tremendous advances in the field of pharmaceuticals, there are, of course, drawbacks to the administration of any given pharmaceutical agent. Sometimes, the disadvantages, or "side effects," are so severe as to preclude administration of a particular agent at a therapeutically effective dose. Furthermore, many agents in the same therapeutic class display similar side effect profiles, meaning that patients either have to forego therapy or suffer from varying degrees of side effects associated with the medication of choice.

In U.S. Pat. No. 7,056,890 to Najarian and U.S. Patent Publication Nos. US 2006/0234950 A1, US 2006/0234951 A1, and US 2006/0234952 A1 to Najarian, all of common assignment herewith to Vivus, Inc. (Mountain View, Calif.), a combination therapy for treating obesity and effecting weight loss is provided wherein a synergistic effect between the active agents enables dose reduction and a concomitant alleviation of side effects typically associated with each active agent. One of the active agents is an anti-convulsant agent, e.g., topiramate, and the second active agent is a sympathomimetic agent, typically a sympathomimetic amine such as phentermine. In U.S. patent application Ser. No. 12/135,935, also of common assignment herewith, an escalating dosing regimen is described for administering topiramate alone or in combination with a second therapeutic agent such as phentermine, wherein the second agent is selected so as to directly or indirectly reduce the side effects associated with one or both of the agents administered. By "indirectly" reducing side effects is meant that a first pharmaceutical agent allows the second agent to be administered at a lower dose without compromising therapeutic efficacy, thus reducing dose-dependent unwanted effects.

Topiramate (2,3,4,5-bis-O-(1-methylethylidene)-β-D-fructopyranose sulfamate) is a broad-spectrum neurotherapeutic agent approved by the FDA and the regulatory agencies of many other countries for the treatment of certain seizure disorders and the prevention of migraine headaches. E. Faught et al. (1996) Neurology 46:1684-90; Karim et al. (1995) Epilepsia 36 (S4):33; S. K. Sachdeo et al. (1995) Epilepsia 36(S4):33; T. A. Glauser (1999) Epilepsia 40 (S5): S71-80; R. C. Sachdeo (1998) Clin. Pharmacokinet. 34:335-346). There has also been evidence that topiramate is effective in the treatment of diabetes (U.S. Pat. Nos. 7,109,174 and 6,362,220), neurological disorders (U.S. Pat. No. 6,908,902), depression (U.S. Pat. No. 6,627,653), psychosis (U.S. Pat. No. 6,620,819), headaches (U.S. Pat. No. 6,319,903) and hypertension (U.S. Pat. No. 6,201,010). However there have been adverse effects associated with the use of topiramate in humans, such as cognitive dulling and word finding difficulties, which can discourage many obese patients from taking this drug.

Phentermine was approved by the FDA as an appetite suppressant in 1959, and phentermine hydrochloride has been used as a weight loss agent since the 1970s, e.g., under the brand names Adipex-P®, Fastin®, Zantril®, and others. Although the FDA warned against combining phentermine with a second active agent following the reports of cardiac and pulmonary problems associated with the "Fen-Phen" product (in which phentermine was combined with fenfluramine, and later with a related drug, dexfenfluramine), it has since been found that a safe and effective weight loss treatment is provided by combining phentermine with an active agent that mitigates phentermine's side effects and enables administration of a much lower dose of phentermine than in "Fen-Phen" (containing 30 mg or 37.5 mg phentermine hydrochloride). See U.S. Pat. No. 7,056,890 to Najarian and U.S. Patent Publication Nos. US 2006/0234950 A1, US 2006/0234951 A1, and US 2006/0234952 A1 to Najarian, cited above.

It has now been discovered that a significantly lower dose combination product is effective in achieving weight loss, treating obesity, and treating conditions associated with obesity and excessive weight. The present invention is directed to this product and methods of using the product. The invention provides a number of important advantages vis-à-vis prior weight loss therapies, as will be described in detail herein.

SUMMARY OF THE INVENTION

Accordingly, in a first embodiment, the present invention is directed to a method for effecting weight loss in a subject by administering continually over a significant period of time a daily dose of phentermine in the range of 2 mg to 8 mg and in combination therewith a daily amount of topiramate selected to prevent the loss of effectiveness of phentermine alone. Generally, the combination of these active agents is administered orally. The agents may be administered at different times of day, with the phentermine administered earlier in the day and the topiramate administered later in the day, in the afternoon or evening. Normally, however, the two agents are administered simultaneously using one or more dosage forms that provide for immediate release of the phentermine and controlled release of the topiramate. In an exemplary embodiment, the phentermine and topiramate are administered in a single dosage form that provides for immediate release of the phentermine and both delayed and sustained release of the topiramate.

In another embodiment, the invention is directed to a method for effecting weight loss in a subject by administering continually over a significant period of time a daily dose of 3.75 mg phentermine and, in combination therewith, a daily dose of 23 mg topiramate.

In another embodiment, the invention is directed to a method for effecting weight loss in a subject by administering continually over a significant period of time a daily dose of 7.5 mg phentermine and, in combination therewith, a daily dose of 46 mg topiramate.

In these methods, the daily doses of topiramate and phentermine may also be administered to treat one or more conditions associated with excess weight or obesity. These conditions include, without limitation, diabetes, respiratory disorders, gallbladder disease, dyslipidemia, orthopedic problems, reflux esophagitis, snoring, sleep apnea, menstrual irregularities, infertility, pregnancy complications, gout, cardiovascular problems, muscular dystrophy, metabolic disorders, and certain cancers. Accordingly, in a further embodiment, the invention relates to a method as enumerated above which further involves simultaneously treating the subject for a condition associated with excess weight or obesity.

In another embodiment, a composition is provided for administration to a subject in order to effect weight loss, wherein the composition contains 2 mg to 5 mg phentermine and 17 mg to 23 mg topiramate. An exemplary such composition contains 3.75 mg phentermine and 23 mg topiramate. Generally, the composition is an orally administrable unit dosage form that contains both active agents. Certain dosage forms of the invention provide for immediate release of the phentermine and controlled release of the topiramate.

In a further embodiment, a packaged pharmaceutical preparation is provided that contains a composition of the invention in a sealed container, with instructions for administration, typically self-administration, of the composition. Generally, the packaged preparation contains a plurality of orally administrable unit dosage forms, with, preferably, each individual dosage form in a separate sealed housing, e.g., as in a blister pack.

In still another embodiment, the method, composition, and packaged preparation of the invention are adapted to administer phentermine and topiramate to treat epilepsy.

In still another embodiment, the method, composition, and packaged preparation of the invention are adapted to administer phentermine and topiramate to treat an impulse control disorder.

In still another embodiment, the method, composition, and packaged preparation of the invention are adapted to administer phentermine and topiramate to treat a psychiatric disorder such as depression, panic syndrome, generally anxiety disorder, phobic syndromes, mania, manic depressive illness, hypomania, unipolar depression, stress disorders including post-traumatic stress disorder ("PTSD"), somatoform disorders, personality disorders, psychosis, and schizophrenia.

In still another embodiment, the method, composition, and packaged preparation of the invention are adapted to administer phentermine and topiramate to treat adolescent and juvenile obesity.

DETAILED DESCRIPTION OF THE INVENTION

Definitions and Nomenclature

Figure 1:
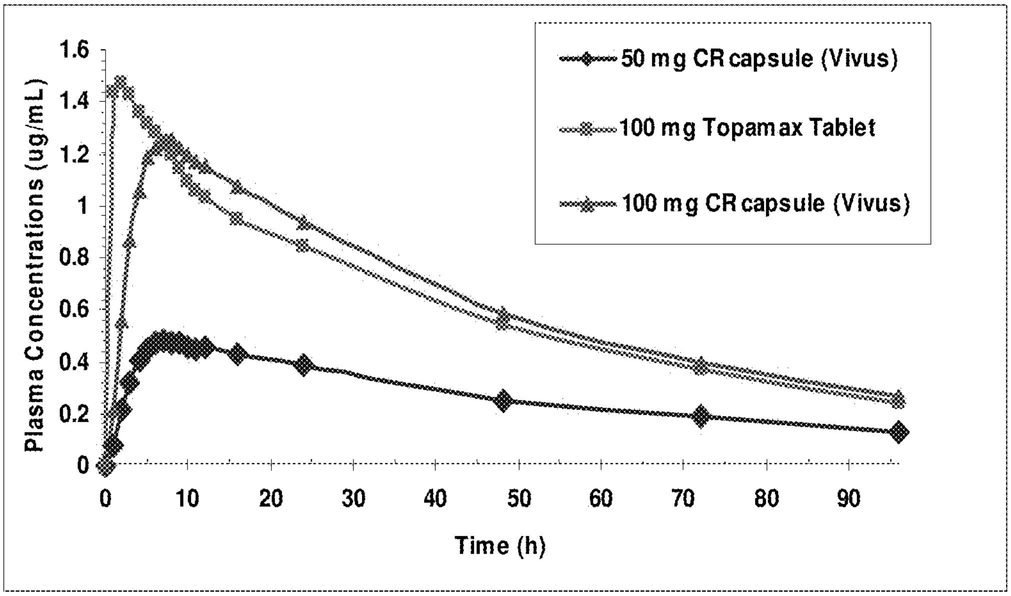
FIG. 1 provides a summary of the plasma concentration of controlled release topiramate according to the present invention versus topiramate (Topamax®) in normal obese subjects.

It must be noted that, as used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

Unless defined otherwise, all technical and scientific terms used herein have the meaning commonly understood by one of ordinary skill in the art to which the invention pertains. Specific terminology of particular importance to the description of the present invention is defined below.

When referring to an active agent, applicants intend the term "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds as will be discussed infra. Therefore, reference to "phentermine" encompasses not only phentermine per se but also salts and other derivatives of phentermine, e.g., phentermine hydrochloride. It is to be understood that when amounts or doses of phentermine are specified, that those amounts or doses refer to the amount or dose of phentermine per se and not to a phentermine salt or the like. For example, when it is indicated that a dose or amount of phentermine is 3.75 mg, that would correspond to 4.92 phentermine hydrochloride and not 3.75 phentermine hydrochloride.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a subject" refers to the process of introducing a composition or dosage form of the invention into the subject (e.g., a human or other mammalian subject) via an art-recognized means of introduction By the terms "effective amount" and "therapeutically effective amount" of an agent, compound, drug, composition or combination of the invention which is nontoxic and effective for producing some desired therapeutic effect upon administration to a subject or patient (e.g., a human subject or patient).

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release, modified release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient provides a measurable time delay before drug is released from the formulation into the patient's body.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "subject" or "individual" or "patient" refers to any subject for whom or which therapy is desired, and generally refers to the recipient of the therapy to be practiced according to the invention. The subject can be any vertebrate, but will typically be a mammal. If a mammal, the subject will in many embodiments be a human, but may also be a domestic livestock, laboratory subject or pet animal.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Methods and Formulations of the Invention:

The present invention provides novel methods and compositions to effect weight loss and treat obesity, conditions related to excess weight or obesity, diabetes (whether or not related to obesity), and other conditions and disorders as will be explained infra. According to the U.S. Centers for Disease Control, the clinical definition of being overweight (the term being used synonymously herein with the term "excess weight") is having a body mass index (BMI) between 25.0 and 29.9 kg/m; BMI is calculated by multiplying an individual's weight, in kilograms, by height, in meters. The CDC defines obesity as having a BMI of 30 or higher. In one embodiment, the invention provides a method for effecting weight loss and treating overweight, obesity, and conditions associated with excess weight and obesity, and involves administration of a combination of the sympathomimetic agent phentermine and the anti-convulsant agent topiramate.

Topiramate is an anticonvulsant sulfamate compound that is sold in the United States under the trade name Topamax® (Ortho-McNeil Pharmaceutical, Inc., Raritan, N.J., U.S.A). Topiramate has been approved for use as an antiepileptic agent as an adjuvant therapy for patients with partial onset seizures or primary generalized tonic-clonic seizures, and for the prevention of migraine headache. See Physician's Desk Reference, 56th ed. (2002); see also U.S. Pat. No. 4,513,006 to Maryanoff et al. and U.S. Pat. No. 7,351,695 to Almarssoo et al.

"Topiramate" generally refers to the sulfamate-substituted monosaccharide having the chemical name 2,3,4,5-bis-O-(1-methylethylidene)-β-D-fructopyranose sulfamate and the molecular formula $C12H21NO8S$. The structure of the compound is represented by Formula (I)

(I)

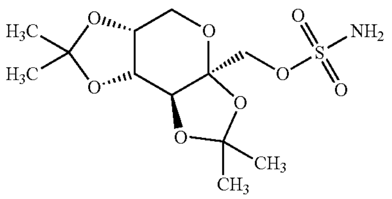

As used herein, the term "topiramate" encompasses 2,3,4,5-bis-(O)-(1-methylethylidene)-β-D-fructopyranose sulfamate as well as individual enantiomers, individual diastereomers, or mixtures thereof. The term "topiramate" as used herein also encompasses topiramate salts as well as polymorphs, solvates (including hydrates and mixed solvates, as well as hydrates of salts), co-crystals (for instance, with other compounds or other forms of topiramate), amorphous, and anhydrous forms of the compound of Formula (I). Topiramate salts useful in conjunction with the present invention, as will be appreciated from the fact that the compound is a sulfamic acid derivative, are pharmaceutically acceptable basic addition salts. Such salts are prepared from bases that provide a pharmaceutically acceptable cation that associates with the sulfamic acid group of the compound of Formula (I). Suitable pharmaceutically acceptable cations include both organic and inorganic cations, including, without limitation, sodium, sodium, potassium, lithium, magnesium, calcium, aluminum, zinc, procaine, benzathine, chloroprocaine, choline, diethylamine, ethylenediamine, N-methylglucamine, benethamine, clemizole, diethylamine, piperazine, tromethamine, triethylamine, ethanolamine, triethanolamine, arginine, lysine, histidine, tributylamine, 2-amino-2-pentylpropanol, 2-amino-2-methyl-1,3-propanediol, tris(hydroxymethyl) aminomethane, benzylamine, 2-(dimethylamino)ethanol, barium or bismuth counter ions. Particularly preferred cations are sodium, lithium, and potassium. Other forms of topiramate referenced above may be prepared using methods known in the art; see, e.g., U.S. Pat. No. 7,351,695.

At dosages previously believed to be required for therapeutic efficacy, administration of topiramate has been associated with significant adverse effects, as noted above, including, without limitation, dizziness, psychomotor slowing, difficulty with memory, fatigue, and somnolence. See U.S. Pat. No. 7,351,695, supra, and Physicians' Desk Reference, supra.

Phentermine is a sympathomimetic agent that has been used as an appetite suppressant, but, like topiramate, has been associated with significant adverse effects at doses previously believed to be required for efficacy; these effects are generally associated with the catecholamine-releasing properties of the drug, including, for instance, tachycardia, elevated blood pressure, anxiety, and insomnia. Phentermine is a shortened version of the compound's chemical name, phenyl-tertiary-butylamine, and is also referred to as 2-methyl-1-phenylpropan-2-amine and 2-methyl-amphetamine. Phentermine has the molecular formula $C_{10}H_{15}N$, the chemical structure of Formula (II)

(II)

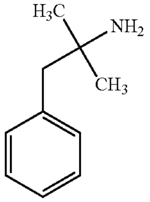

and is an achiral primary amine. As such, phentermine may be in the form of either the free base or an acid addition salt prepared with an acid that yields a pharmaceutically acceptable anion. Suitable acid addition salts may be prepared from organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, etc. As with topiramate, phentermine may take on various other forms as well.

It has now been surprisingly discovered that a combination of a low daily dose of topiramate and a low daily dose of phentermine is effective in achieving weight loss, treating obesity, treating conditions related to overweight and obesity, and addressing other indications as will be discussed herein. The incidence of adverse effects previously associated with each active agent is significantly reduced because of the lowered daily dosage as well as the offsetting effect each active agent has on the potential adverse effects of the other active agent. Even at the low doses of the present methods, phentermine has anorexient properties (e.g., suppresses appetite) and is anorectic without loss of efficacy or without adverse or undesirable side effects to a subject when administered according to the dosage regimens described herein when the phentermine is administered in combination with topiramate.

The present method for effecting weight loss in a subject involves administering a daily dose of phentermine in the range of 2 mg to 8 mg, e.g., 2 mg to 5 mg, in combination with a daily dose of topiramate selected to prevent the loss of effectiveness of phentermine alone. An example of a suitable daily dose of topiramate that would prevent the loss of effectiveness of phentermine alone is 15 mg to 50 mg, e.g., 15 mg to 25 mg or 17 mg to 23 mg. An exemplary dosage regimen involves administration of daily doses of 3.75 mg phentermine and 23 mg topiramate. Another exemplary dosage regimen involves administration of daily doses of 7.5 mg and 46 mg topiramate.

When the topiramate and/or the phentermine are associated with additional moieties, e.g., are in the form of salts, hydrates, or the like, the dosage herein refers to the compound per se and does not include the associated moieties, e.g., cations, anions, hydrates, etc. Thus, if phentermine hydrochloride is used in the methods and compositions of the invention, 4.92 mg of phentermine hydrochloride (having a molecular weight of 195.69 g/mol) will be necessary to provide the 3.75 mg daily dose of phentermine (having a molecular weight of 149.23 g/mol).

The dosage regimen involves continual, i.e., ongoing, administration, over a significant period of time, e.g., in the range of about 4 weeks to about 67 weeks, depending on the severity of an individual's weight problem, the amount of weight that should be lost, and the rate at which weight is lost.

Generally, although not necessarily, the combination of the active agents is administered orally.

The method of administration can involve simultaneous administration of the two active agents, in a single composition or in two discrete compositions each containing one of the active agents. The method of administration may also involve administration of the two active agents at different times of day, with the phentermine generally administered earlier in the day and the topiramate generally administered later in the day. Normally, however, the two agents are administered simultaneously using one or more dosage forms that provide for immediate release of the phentermine and controlled release of the topiramate. In an exemplary embodiment, the phentermine and topiramate are administered in a single dosage form that provides for immediate release of the phentermine and sustained release and/or delayed release of the topiramate.

Examples of compositions that contain a combination of phentermine and topiramate include, without limitation: (1) 2 mg to 5 mg phentermine and 17 mg to 23 mg topiramate; (2) 3.75 mg phentermine and 23 mg topiramate; (3) 3.75 mg phentermine in the form of 4.92 mg phentermine hydrochloride and 23 mg topiramate; (4) 7.5 mg phentermine and 46 mg topiramate; and (5) 7.5 mg phentermine in the form of 9.84 mg phentermine hydrochloride and 46 mg topiramate.

These and other compositions of the invention exhibit a lower maximum concentration (Cmax) of topiramate without decreasing total drug exposure defined by the area under the concentration-time curve (AUC). Further, preferred compositions of the present invention can provide for delayed, sustained release of topiramate such that the maximum plasma concentration (Tmax) is reached 6 to 10, typically 6 to 8, hours after administration. As depicted in FIG. 1, drug exposure as measured by AUC for a controlled release (CR) formulation capsule prepared as described in Example 1 is the same as that observed with an immediate release topiramate (Topamax®) tablet despite a 20% reduction in the Cmax. Therefore, formulations of the invention are capable of reducing the Cmax of topiramate, enabling a reduction in side effects without compromising the efficacy of the treatment, since the AUC is the same. This reduction in Cmax is preferred as topiramate can be sedating, as noted above, and a delay in the time to reach maximum plasma concentration to the late afternoon or evening time improves the tolerability of the drug. On the other hand, the preferred formulations of the invention provide for immediate release of phentermine, with the medication administered early in the day, such that any stimulant effects that may be experienced do not occur in the evening.

In another embodiment of the invention, a composition is provided that contains 7.5 mg phentermine and 46 mg topiramate.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). Oral administration and therefore oral dosage forms are generally preferred, and include tablets, capsules, caplets, solutions, suspensions and syrups, and may also comprise a plurality of granules, beads, powders, or pellets that may or may not be encapsulated. Preferred oral dosage forms are capsules and tablets, particularly controlled release capsules and tablets, as noted above.

As noted above, it is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of topiramate, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited earlier herein, which describes materials and methods for preparing encapsulated pharmaceuticals.

Oral dosage forms, whether tablets, capsules, caplets, or particulates, can, if desired, be formulated so as to provide for controlled release of topiramate, and in a preferred embodiment, the present formulations are controlled release oral dosage forms. Generally, the dosage forms provide for sustained release, i.e., gradual, release of topiramate, from the dosage form to the patient's body over an extended time period, typically providing for a substantially constant blood level of the agent over a time period in the range of about 4 to about 12 hours, typically in the range of about 6 to about 10 hours or 6 to about 8 hours. Release of the topiramate may also be delayed; that is, there is a time lag between administration and the start of topiramate release. In this way, for instance, an individual will not experience sleepiness or other side effects of topiramate during the school or work day. Preferred dosage forms thus involve sustained release of the topiramate, delayed release of the topiramate, or both sustained and delayed release of the topiramate.

Generally, as will be appreciated by those of ordinary skill in the art, sustained release dosage forms can be formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone e.g., Povidone K30, polyvinyl acetate, and ethylene-vinyl acetate copolymer. Preferred sustained release polymers herein include those available as "Methocel" polymers from Dow Chemical, particularly the methylcellulose ether polymers in the Methocel™ A group, having a viscosity grade of about 4,000 cps and a methoxyl content of about 27.5% to 31.5%, e.g., Methocel™ A15LV, Methocel™ A15C, and Methocel™ A4M.

When sustained release preparations are prepared, tablets, granules, powder, capsules, and the like can be produced according to a conventional method after adding excipient, and as necessary, binder, disintegrating agent, lubricant, coloring agent, taste-modifying agent, flavoring agent, and the like. These additives may be ones generally used in the field, and for example, lactose, sodium chloride, glucose, starch, microcrystalline cellulose, and silicic acid as the excipient, water, ethanol, propanol, simple syrup, gelatin solution, hydroxypropyl cellulose, methyl cellulose, ethyl cellulose, shellac, calcium phosphate, and polyvinylpyrrolidone as the binder, agar powder, sodium hydrogen carbonate, sodium lauryl sulfate, and stearic acid monoglyceride as the disintegrating agent, purified talc, stearic acid salt, borax, and polyethylene glycol as the lubricant, β-carotene, yellow iron sesquioxide, and caramel as the coloring agent, and saccharose and orange peel as the taste-modifying agent can be listed as examples. It should be noted that various grades of microcrystalline cellulose are preferred fillers herein, e.g., Avicel® PH101, Avicel® PH102, and Avicel® PH200 (FMC), with particle sizes of about 50 microns, 100 microns, and 190 microns, respectively. Microcrystalline cellulose having a particle size in the range of about 50 microns to 200 microns is preferred herein.

The dosage forms may also be provided with a delayed release coating, e.g., composed of an acrylate and/or methacrylate copolymers. Examples of such polymers are those available under the trade name "Eudragit" from Rohm Pharma (Germany). The Eudragit series E, L, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Other preferred Eudragit polymers are cationic, such as the Eudragit E, RS, and RL series polymers. Eudragit E100 and E PO are cationic copolymers of dimethylaminoethyl methacrylate and neutral methacrylates (e.g., methyl methacrylate), while Eudragit RS and Eudragit RL polymers are analogous polymers, composed of neutral methacrylic acid esters and a small proportion of trimethylammonioethyl methacrylate.

In a specific embodiment, controlled release topiramate beads for oral administration, e.g., by incorporation in an orally administrable capsule or compaction into an orally administrable tablet, are made using an extrusion spheronization process to produce a matrix core comprised of: topiramate, 40.0% w/w; microcrystalline cellulose, e.g., Avicel® PH102, 56.5% w/w; and methylcellulose, e.g., Methocel™ A15 LV, 3.5% w/w. The topiramate cores are then coated with ethyl cellulose, 5.47% w/w and Povidone K30: 2.39% w/w. The phentermine beads are composed of an immediate release drug coating onto sugar spheres or analogous non-active cores. Both sets of beads may then be encapsulated into one capsule.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The active agents may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agent may be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, or via an implanted depot, other modes of administration are suitable as well. For example, administration may be transmucosal, e.g., rectal or vaginal, preferably using a suppository that contains, in addition to the active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

Indications:

Conditions of particular interest for which the invention finds utility include overweight, obesity and conditions often associated with and/or caused by excess weight and obesity. The combination of topiramate and phentermine in the dosages provided herein give rise to significant therapeutic effects and reduced adverse effects, making these pharmaceutical combinations extremely effective therapeutics, especially in the treatment of overweight, obesity and/or related conditions, including conditions associated with and/or caused by excess weight or obesity per se. Subjects suitable for treatment with the subject combination therapy treatment regimen thus include individuals suffering from conditions associated with obesity, such conditions including, without limitation:

diabetes, insulin resistance, and impaired glucose tolerance;

respiratory problems such as pulmonary hypertension, asthma, and shortness of breath;

gallbladder disease;

dyslipidemia, e.g., high cholesterol, high levels of triglycerides, etc.;

osteoarthritis and other orthopedic problems;

reflux esophagitis;

adverse conditions related to sleep, including sleep apnea and loud snoring;

menstrual irregularities, infertility, and complications in pregnancy;

gout;

high blood pressure, i.e., hypertension;

cardiovascular problems such as coronary artery disease and other heart trouble;

muscular dystrophy;

stroke, particularly thrombotic stroke and deep vein thrombosis (DVT);

migraines;

metabolic disorders such as hypoalphalipoproteinemia, familial combined hyperlipidemia, and Syndrome X, including insulin-resistant Syndrome X; and colon, rectal, renal, esophageal, gallbladder, pancreatic, prostate, breast, uterine, ovarian, endometrial, and cervical cancers.

Higher body weights are also associated with increases in all-cause mortality. Most or all of these problems are relieved or improved by permanent significant weight loss. Longevity is likewise significantly increased by permanent significant weight loss.

Diabetes mellitus is very commonly seen in obese individuals, and is associated with continuous and pathologically elevated blood glucose concentration. It is one of the leading causes of death in the United States and is responsible for about 5% of all mortality. Diabetes is divided into two major sub-classes: Type I, also known as juvenile diabetes, or Insulin-Dependent Diabetes Mellitus (IDDM); and Type II, also known as adult onset diabetes, or Non-Insulin-Dependent Diabetes Mellitus (NIDDM).

According to the American Diabetes Association, there are over one million juvenile diabetics in the United States. Type I Diabetes is a form of autoimmune disease. Autoantibodies produced by the patients completely or partially destroy the insulin producing cells of the pancreas. Juvenile diabetics must, therefore, receive exogenous insulin during their lifetime. Without treatment, excessive acidosis, dehydration, kidney damage, and death may result. Even with treatment, complications such as blindness, atherosclerosis, and impotence can occur.

There are more than five million Type II (adult onset) diabetics diagnosed in the United States. Type II disease usually begins during middle age; the principal cause is now known to be overweight and obesity. In Type II diabetics, rising blood glucose levels after meals do not properly stimulate insulin production by the pancreas. Additionally, peripheral tissues are generally resistant to the effects of insulin. The resulting high blood glucose levels (hyperglycemia) can cause extensive tissue damage. Type II diabetics are often referred to as insulin resistant. They often have higher than normal plasma insulin levels (hyperinsulinemia) as the body attempts to overcome its insulin resistance. Some researchers now believe that hyperinsulinemia may be a causative factor in the development of high blood pressure, high levels of circulating low density lipoproteins (LDLs), and lower than normal levels of the beneficial high density lipoproteins (HDLs). While moderate insulin resistance can be compensated for in the early stages of Type II diabetes by increased insulin secretion, in more advanced disease states insulin secretion is also impaired.

Insulin resistance and hyperinsulinemia have also been linked with two other metabolic disorders that pose considerable health risks: impaired glucose tolerance and metabolic obesity. Impaired glucose tolerance is characterized by normal glucose levels before eating, with a tendency toward elevated levels (hyperglycemia) following a meal. According to the World Health Organization, approximately 11% of the U.S. population between the ages of 20 and 74 are estimated to have impaired glucose tolerance. These individuals are considered to be at higher risk for diabetes and coronary artery disease.

Obesity may also be associated with insulin resistance. A causal linkage among obesity, impaired glucose tolerance, and Type II diabetes has been proposed, but a physiological basis has not yet been established. Some researchers believe that impaired glucose tolerance and diabetes are clinically observed and diagnosed only later in the disease process after a person has developed insulin resistance and hyperinsulinemia.

Insulin resistance is frequently associated with hypertension, coronary artery disease (arteriosclerosis), and lactic acidosis, as well as related disease states. The fundamental relationship between these disease states, and a method of treatment, has not been established.

Hypertension is another condition that is frequently seen in obese individuals, and occurs when the blood pressure inside the large arteries is chronically elevated. Hypertension affects about 50 million people in the United States alone. It is more common as people grow older and is both more common and more serious in African Americans. Most cases of hypertension are of unknown etiology. It is known that the tendency to develop hypertension can be inherited. Environment also plays a very important role in hypertension. For example, hypertension may be avoided by keeping body weight under control, keeping physically fit, eating a healthy diet, limiting alcohol intake, and avoiding medications that might increase blood pressure. Other less common causes of hypertension include disorders of the kidneys or endocrine glands. Hypertension has been called "the silent killer" because it has no specific symptoms and yet can lead to death. People with untreated hypertension are much more likely to die from or be disabled by cardiovascular complications such as strokes, heart attacks, heart failure, heart rhythm irregularities, and kidney failure, than people who have normal blood pressure.

Current treatments for hypertension include lifestyle changes (diet, exercise, nonsmoking, etc.) as well as drug therapy. The major classes of medications currently used to treat hypertension include adrenergic neuron antagonists (which are peripherally acting), alpha adrenergic agonists (which are centrally acting), alpha adrenergic blockers, alpha and beta blockers, angiotensin II receptor blockers, angiotensin converting enzyme (ACE) inhibitors, beta adrenergic blockers, calcium channel blockers, thiazides (benzothiadiazine derivatives) and related diuretics, and vasodilators (which act by direct relaxation of vascular smooth muscles).

A particularly serious hypertensive disorder is primary pulmonary hypertension, also known as idiopathic pulmonary hypertension. This is a condition in which the blood pressure in the pulmonary arteries is abnormally high in the absence of other diseases of the heart or lungs. The cause of primary pulmonary hypertension is unknown. Pulmonary hypertension develops in response to increased resistance to blood flow. Narrowing of the pulmonary arterioles occurs and the right side of the heart becomes enlarged due to the increased work of pumping blood against the resistance. Eventually, progressive heart failure develops. Currently, there is no known cure for primary pulmonary hypertension. Treatment is primarily directed towards controlling the symptoms, although some success has occurred with the use of vasodilators. Other medications used to treat the symptoms of primary pulmonary hypertension include diuretics and calcium channel blockers. Typically, as the disease progresses, oxygen is often required. In certain cases, a heart-lung transplant may be indicated for certain suitable candidates, although the availability of donor organs continues to be extremely limited. Unfortunately, primary pulmonary hypertension is a progressive disease, usually leading to congestive heart failure and respiratory failure.

Secondary pulmonary hypertension is a serious disorder that arises as a complication of other conditions such as, for example, scleroderma. Treatments are similar as those for primary pulmonary hypertension and, unfortunately, the prognosis is the same as well.

Other respiratory disorders that are frequently seen in obese individuals include asthma and shortness of breath, both of which conditions are often alleviated by weight loss.

With respect to adverse conditions and disorders associated with sleep, sleep apnea is perhaps the most concerning. Sleep apnea is classified as either obstructive sleep apnea, the more common form that occurs when throat muscles relax, or central sleep apnea, which occurs when the brain doesn't send proper signals to the muscles that control breathing. Additionally, some people have mixed sleep apnea, which is a combination of both obstructive and central sleep apneas. Sleep apnea literally means "cessation of breath." It is characterized by repetitive episodes of upper airway obstruction that occur during sleep, usually associated with a reduction in blood oxygen saturation. In other words, the airway becomes obstructed at several possible sites. The upper airway can be obstructed by excess tissue in the airway, large tonsils, and a large tongue and usually includes the airway muscles relaxing and collapsing when asleep. Another site of obstruction can be the nasal passages. Sometimes the structure of the jaw and airway can be a factor in sleep apnea.

The signs and symptoms of obstructive and central sleep apneas overlap, sometimes making the type of sleep apnea more difficult to determine. The most common signs and symptoms of obstructive and central sleep apneas include: excessive daytime sleepiness (hypersomnia); loud snoring; observed episodes of breathing cessation during sleep; abrupt awakenings accompanied by shortness of breath; awakening with a dry mouth or sore throat; morning headache; and/or difficulty staying asleep (insomnia). Disruptive snoring may be a more prominent characteristic of obstructive sleep apnea, while awakening with shortness of breath may be more common with central sleep apnea.

Sleep apnea is a progressive condition and can be very serious; it is a potentially life-threatening condition that requires immediate medical attention. The risks of undiagnosed obstructive sleep apnea include heart attacks, strokes, high blood pressure, heart disease, irregular heartbeat, and impotence. In addition, obstructive sleep apnea causes daytime sleepiness that can result in accidents, lost productivity and interpersonal relationship problems. The severity of the symptoms may be mild, moderate or severe.

Sleep apnea is diagnosed utilizing a sleep test, called polysomnography but treatment methodologies differ depending on the severity of the disorder. Mild Sleep Apnea is usually treated by some behavioral changes; losing weight and sleeping on one's side are often recommended. There are oral mouth devices (that help keep the airway open) that may help to reduce snoring in three different ways. Some devices (1) bring the jaw forward or (2) elevate the soft palate or (3) retain the tongue (from falling back in the airway and blocking breathing).

Moderate to severe sleep apnea is usually treated with a continuous positive airway pressure (C-PAP). C-PAP is a machine that blows air into your nose via a nose mask, keeping the airway open and unobstructed. For more severe apnea, there is a Bi-level (Bi-PAP) machine. The Bi-level machine is different in that it blows air at two different pressures. When a person inhales, the pressure is higher and in exhaling, the pressure is lower.

Some people have facial deformities that may cause the sleep apnea. It simply may be that their jaw is smaller than it should be or they could have a smaller opening at the back of the throat. Some people have enlarged tonsils, a large tongue or some other tissues partially blocking the airway. Fixing a deviated septum may help to open the nasal passages. Removing the tonsils and adenoids or polyps may help also. Children are much more likely to have their tonsils and adenoids removed. Surgical procedures, such as tracheotomy, uvulopalatopharyngoplasty (UPPP), laser assisted uvuloplasty (LAUP), somnoplasty, and mandibular myotomy are often required to effectively treat sleep apnea. Weight loss, however, particularly in an obese person, can significantly alleviate sleep apnea and other sleep-related adverse conditions such as loud snoring and the like.

Relatively recently, a connection between obesity and the occurrence or increased incidence of migraine headaches has been noted. Migraine headaches begin with mild pain, which increases in intensity over a short period of time. There are two major types of migraines. The common migraine affects 80-85% of migraine sufferers and classical migraine with aura affects 15% of migraine sufferers. Symptoms associated with migraines include headaches, psychological symptomology such as irritability, depression, fatigue, drowsiness, restlessness; neurological symptoms such as photophobia, phonophobia or gastrointestinal symptoms such as change in bowel habit, change of food intake or urinary symptoms such as urinary frequency, auras which are neurological deficits and can be a variety of deficits for the migraine population but in the individual is usually stereotyped. These deficits may be visual scotoma or visual designs, hemiplegia, migrating paraesthesia, dysarthria, dysphasia, or déjà vu. The headache is usually accompanied by light or sound sensitivity, photophobia or phonophobia, irritability and impaired concentration. For those individuals whose migraine headaches are caused by or exacerbated by obesity, treatment according to the methodology of the present invention can be effective.

Other indications for which the present invention is readily adapted include epilepsy and certain psychiatric indications such as impulse control disorders.

Topiramate has long been known as an anti-epileptic agent. At dosages previously required or believed to be required for efficacy, however, topiramate therapy resulted in significant side effects, as noted elsewhere herein. The present invention, according to which topiramate dosage may be reduced by concomitant administration of phentermine, significantly reduces those side effects of topiramate, most if not all of which are dose-related.

Among psychiatric indications, depression is particularly common. “Depression,” as is well known, is manifested by a combination of symptoms that interfere with the ability to work, study, sleep, eat, and enjoy once pleasurable activities. Depression includes major depression, especially refractory depression, bipolar depression, and the degeneration associated with depression. Symptoms of depression include persistent sad, anxious, or “empty” mood, feelings of hopelessness, pessimism, feelings of guilt, worthlessness, helplessness, loss of interest or pleasure in hobbies and activities that were once enjoyed, including sex, decreased energy, fatigue, being “slowed down”, difficulty concentrating, remembering, making decisions, insomnia, early-morning awakening, or oversleeping, appetite and/or weight loss or overeating and weight gain, thoughts of death or suicide; suicide attempts, restlessness, irritability, persistent physical symptoms that do not respond to treatment, such as headaches, digestive disorders, and chronic pain.

Other psychiatric disorders may also be treated using the compositions and methods of the invention. These disorders include impulse control disorders, panic syndrome, general anxiety disorder, phobic syndromes of all types, mania, manic depressive illness, hypomania, unipolar depression, stress disorders, PTSD, somatoform disorders, personality disorders, psychosis, and schizophrenia.

“Impulse Control Disorders” are characterized by harmful behaviors performed in response to irresistible impulses. The essential feature of an impulse control disorder is the failure to resist an impulse, drive, or temptation to perform an act that is harmful to the person or to others. Symptoms include an increasing sense of tension or arousal before committing an act, and then experiences pleasure, gratification, or release at the time of committing the act. After the act is performed, there may or may not be regret or guilt. Numerous disorders can be characterized as impulse control disorders including intermittent explosive disorder, kleptomania, pathological gambling, pyromania, trichotillomania, compulsive buying or shopping, repetitive self-mutilation, nonparaphilic sexual addictions, severe nail biting, compulsive skin picking, personality disorders with impulsive features, attention deficit/hyperactivity disorder, eating disorders characterized by binge eating, and substance abuse disorders such as alcoholism and drug addiction. Binge eating disorder and bulimia are also sometimes classified as impulse control disorders.

Packaged Pharmaceutical Preparations:

Also provided are packaged pharmaceutical preparations for practicing the subject methods. The packaged preparation contains a composition of the invention in a sealed container, and typically contains a plurality of individual dosage forms each in a sealed housing, as in a blister pack, but could also contain one or more dosage forms in a single sealed container. The dosage forms might be, for instance, dosage forms containing 3.75 mg phentermine in immediate release form and 23 mg topiramate in controlled release form, or, in an alternative example, 7.5 mg phentermine in immediate release form and 46 mg topiramate in controlled release form. Optionally, dosage forms with lower doses of one or both active agents can also be included, for dose titration and dose escalation.

In certain embodiments, the packaged pharmaceutical preparations include instructions for a patient to carry out drug administration to achieve weight loss, treat obesity, treat conditions associated with obesity, or treat other conditions as explained earlier herein. For instance, the instructions may include the daily dose of topiramate to be taken, the daily dose of phentermine to be taken, and/or the dosing regimen for self-administration of a controlled release dosage form containing both active agents. The instructions may be recorded on a suitable recording medium or printed on a substrate such as paper or plastic. As such, the instructions may be present as a package insert, in the labeling of the package, container(s), or components thereof (i.e., associated with the packaging or sub-packaging), etc. In other embodiments, the instructions are present as an electronic storage data file present on a suitable computer readable storage medium, e.g. CD-ROM, diskette, etc. In yet other embodiments, the actual instructions are not present, but means for obtaining the instructions from a remote source, e.g. via the internet, are provided. As an example, a web address might be included to direct patients to a website where the instructions can be viewed and/or from which the instructions can be downloaded. As with the instructions per se, this means for obtaining the instructions is recorded on a suitable substrate.

Some or all of the included components may be packaged in suitable packaging to maintain sterility. In many embodiments, the components are packaged in a containment element to provide a single, easily handled unit, where the containment element, e.g., box or analogous structure, may or may not be an airtight container, e.g., to further preserve the sterility of some or all of the components. In certain aspects, a sealed package of controlled release dosage forms is provided wherein the dosage forms contain phentermine in immediate release form and topiramate in controlled release, e.g., sustained release and delayed release form. Alternatively, separate phentermine-containing and topiramate-containing dosage forms may be included.

This invention is further illustrated by the following examples which should not be construed as limiting. Although any methods and materials similar or equivalent to those described herein may be useful in the practice or testing of the present invention, preferred methods and materials are described below.

The contents of all references, patents and published patent applications cited throughout this application are hereby incorporated by reference.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Controlled release topiramate beads are made using an extrusion spheronization process to produce a matrix core comprised of topiramate, 40.0% w/w; microcrystalline cellulose (Avicel® PH102), 56.5% w/w; and Methocel™ A15 LV, 3.5% w/w. The topiramate cores were then coated with ethyl cellulose, 5.47% w/w, and Povidone K30, 2.39% w/w.

The composition of the topiramate beads so prepared is as follows:

| Component | % w/w |
|---|---|
| topiramate | 36.85 |
| microcrystalline cellulose, (Avicel ® PH102) | 52.05 |
| Methylcellulose (Methocel ™ A15 LV) | 3.22 |
| ethylcellulose | 5.47 |
| Polyvinylpyrrolidone (Povidone K30) | 2.39 |

Phentermine hydrochloride is coated onto sugar spheres to provide immediate release phentermine beads. Both sets of beads are then encapsulated into each of a plurality of capsules, with each capsule containing 3.75 mg phentermine (as 4.92 mg phentermine HCl) and 23 mg topiramate.

Example 2

Controlled release topiramate beads and immediate release phentermine beads are prepared as in Example 1. Both sets of beads are then encapsulated into each of a plurality of capsules, with each capsule containing 7.5 mg phentermine and 46 mg topiramate.

Example 3

Figure 2:
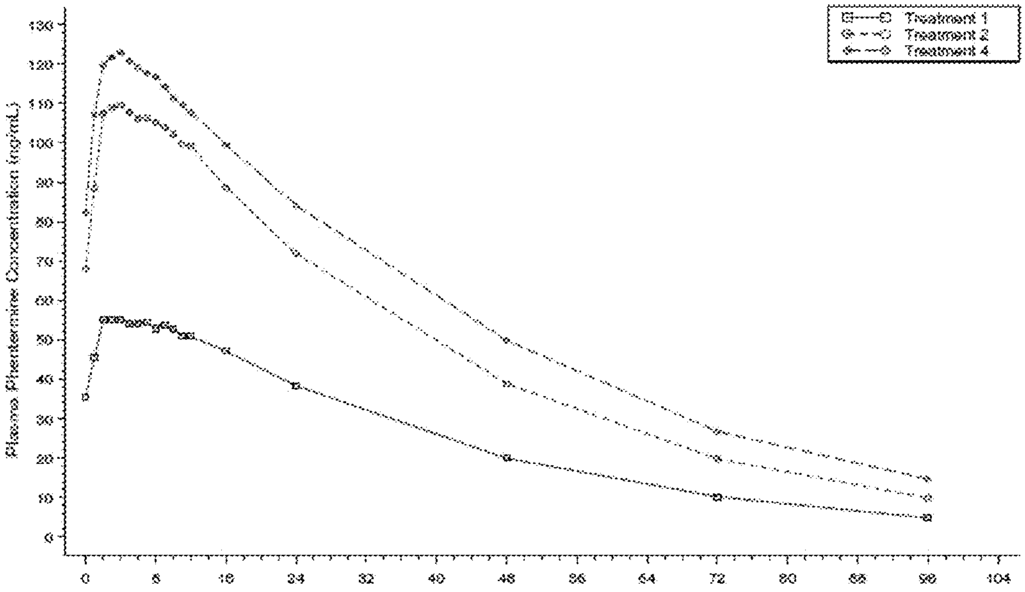
FIG. 2 depicts the mean plasma phentermine concentrations versus time for subjects administered phentermine in combination with controlled release topiramate and phentermine in combination with immediate release topiramate (Topamax®).

In a study comparing controlled-release formulation of topiramate according to the present invention versus immediate release topiramate (Topamax®) in combination with phentermine, the controlled release formulation of the instant invention of topiramate had a 10-15% lower effect on phentermine exposure (FIG. 2).

The mean and statistical comparisons for plasma phentermine PK parameters at steady state in multiple dose administrations are summarized in Table 1.

TABLE 1

Arithmetic Mean (SD) and Statistical Comparison of Pharmacokinetic Parameters for Plasma Phentermine

| | | Treatment 2 Versus Treatment 4 | | |
|---|---|---|---|---|
| Pharmacokinetic Parameters | Mean +/− SD Treatment 2 (N = 13) | Treatment 4 (N = 12) | 90% Confidence Intervals | % Mean Ratio |
| $AUC_{0\text{-}tau}$ (ng * hr/mL) | 2250 +/− 563 | 2530 +/− 644 | (75.6, 105.3) | 89.2 |
| $AUC_{0\text{-}96}$ (ng * hr/mL) | 4640 +/− 1570 | 5550 +/− 1960 | (67.1, 105.0) | 84.0 |
| $AUC_{0\text{-}t}$ (ng * hr/mL) | 4640 +/− 1570 | 5550 +/− 1960 | (67.1, 105.0) | 84.0 |
| $C_{max,ss}$ (ng * hr/mL) | 114 +/− 23.6 | 127 +/− 27.6 | (78.8, 104.5) | 90.7 |
| $C_{min,ss}$ (ng * hr/mL) | 9.84 +/− 7.24 | 14.6 +/− 11.3 | (42.5, 109.0) | 68.1 |
| $t_{max}$ (hr) | 4.01 (1.04, 7.00) | 4.54 (1.00, 10.0) | | |
| $T_{1/2}$ (hr) | 23.3 +/− 6.17 | 26.3 +/− 7.43 | | |
| $CL_{ss}/F$ (L/hr) | 7.10 +/− 1.89 | 6.38 +/− 2.00 | | |
| $V_2/F$ (L/hr) | 229 +/− 45.3 | 232 +/− 58.5 | | |

$t_{max}$ is presented as median (minimum, maximum)

Parameters were dose-normalized and ln-transformed prior to analysis.

% Mean Ratio = 100 * ex[(Treatment 2 − Treatment 4) for ln-transformed parameters Treatment 1 (Test): 7.5 mg phentermine/50 mg topiramate (Formulation A)

Treatment 2 (Test): 15 mg phentermine/100 mg topiramate (Formulation A)

Treatment 4 (Reference): 15 mg phentermine/100 mg topiramate

Source: Tables 14.2.1.8, 14.2.1.10, 14.2.1.12, and 14.2.1.17

These data indicate a lower maximum and extent of phentermine exposure between tests versus reference treatments after multiple-dose administration. As such, the controlled release formulation of topiramate reduced drug interaction with phentermine which in turn will reduce further side effects associated with phentermine.

Example 4

A patient with obesity and elevated lipids exhibiting a heart murmur, shortness of breath out of proportion to weight and age, low blood pressure, leg edema, and a BMI of 46 undergoes an echocardiogram, which shows mitral regurgitation of 1-2+ and mild elevation in pulmonary artery pressure of 36 mm The composition prepared in Example 1 is administered to the patient on a daily basis, and the patient additionally proceeds with a low fat, low carbohydrate diet and daily exercise. Two weeks after the start of her weight loss program she reports that her exercise tolerance is markedly improved and previous chest pressure and shortness of breath on exertion are gone. The patient loses weight continuously on the program and after four months can be expected to lose at least 20 pounds. Ongoing continuation of the program can be expected to result in further weight loss and additional improvement in obesity-related conditions.

Example 5

The procedure of Example 4 is repeated with a second patient having a BMI over 40 and suffering from similar conditions related to obesity.

The composition prepared in Example 2 is administered to the patient on a daily basis, and the patient additionally proceeds with a low fat, low carbohydrate diet and daily exercise. Two weeks after the start of his weight loss program he reports that her exercise tolerance is markedly improved. The patient loses weight continuously on the program and after four months can be expected to lose at least 25 pounds. Ongoing continuation of the program can be expected to result in further weight loss and additional improvement in obesity-related conditions.

The invention claimed is:

1. A unit dosage form for weight loss for oral administration to a patient having a body mass index of at least 25 kg/$m^2$, comprising a combination of:
   an immediate release phentermine formulation containing a unit dosage of phentermine of 3.75 mg or 7.5 mg; and
   a controlled release topiramate formulation containing a unit dosage of topiramate of 23 mg or 46 mg,
   wherein the controlled release topiramate formulation reaches a maximum plasma concentration (Cmax) at about 6 to about 10 hours (Tmax) after administration.

2. The dosage form of claim 1, wherein the subject is overweight having a body mass index between 25 kg/$m^2$ and 29.9 kg/$m^2$.

3. The dosage form of claim 2, wherein the subject has a condition associated with obesity.

4. The dosage form of claim 1, wherein the subject is obese having a body mass index of at least 30 kg/$m^2$.

5. The dosage form of claim 4, wherein the condition associated with obesity is selected from the group consisting of diabetes, elevated fasting blood glucose, insulin resistance, impaired glucose tolerance, pulmonary hypertension, asthma, shortness of breath, gallbladder disease, dyslipidemia, high cholesterol, high levels of triglycerides, osteoarthritis, reflux esophagitis, sleep apnea, menstrual irregularities, infertility, complications in pregnancy, gout, high blood pressure, hypertension, coronary artery disease, heart disease, muscular dystrophy, stroke, thrombotic stroke, deep vein thrombosis (DVT), migraines, metabolic disorders, hypoalphalipoproteinemia, familial combined hyperlipidemia, Syndrome X, insulin-resistant Syndrome X, colon cancer, rectal cancer, renal cancer, esophageal cancer, gallbladder cancer, pancreatic cancer, prostate cancer, breast cancer, uterine cancer, ovarian cancer, endometrial cancer, and cervical cancer.

6. The dosage form of claim 3, wherein the condition associated with obesity is selected from the group consisting of hypertension, dyslipidemia, and type 2 diabetes mellitus.

7. The dosage form of claim 3, wherein the subject is suffering from at least two conditions associated with obesity selected from the group consisting of hypertension, dyslipidemia, and type 2 diabetes mellitus.

8. The dosage form of claim 1, wherein the topiramate formulated for controlled release further exhibits a lower Cmax, than non-controlled release topiramate, without decreasing total drug exposure defined by the area under the concentration-time curve (AUC).

9. The dosage form of claim 1, wherein the unit dosage of phentermine is 3.75 mg and the unit dosage of topiramate is 23 mg.

10. The dosage form of claim 9, wherein the 3.75 mg phentermine is provided in the unit dosage form as about 4.92 mg phentermine hydrochloride, and wherein 4.92 mg of phentermine hydrochloride provides 3.75 mg of phentermine.

11. The dosage form of claim 1, wherein the unit dosage of phentermine is 7.5 mg and the unit dosage of topiramate is 46 mg.

12. The dosage form of claim 11, wherein the 7.5 mg phentermine is provided in the unit dosage form as about 9.84 mg phentermine hydrochloride, and wherein 9.84 mg of phentermine hydrochloride provides 7.5 mg of phentermine.

13. The dosage form of claim 1, wherein following oral administration to a patient, the dosage form provides for a substantially constant blood level of topiramate over a time period in the range of about 4 to about 12 hours.

14. The dosage form of claim 13, wherein the time period is in the range of about 6 to about 10 hours.

15. The dosage form of claim 1, wherein the controlled release topiramate formulation reaches a maximum plasma concentration at about 8 hours to about 10 hours (Tmax) after administration.

16. The dosage form of claim 1, wherein the immediate release phentermine formulation comprises beads of inactive cores coated with the immediate release phentermine formulation.

17. The dosage form of claim 16, comprising a capsule housing the immediate release phentermine beads and the controlled release topiramate beads.

18. The dosage form of claim 1, wherein the controlled release topiramate formulation comprises beads comprising a core comprising topiramate dispersed in a gradually hydrolysable material comprising a binder, and a polymeric filler, and wherein the core is provided with a delayed release coating.

19. The dosage form of claim 18, wherein the delayed release coating comprises one or more of ethylcellulose, hydroxypropyl methylcellulose, microcrystalline cellulose, hydroxypropyl cellulose, polyvinyl acetate, ethylene-vinyl acetate copolymer and polyvinyl pyrrolidone.

20. The dosage form of claim 18, wherein the delayed release coating comprises ethylcellulose and polyvinyl pyrrolidone.

21. The dosage form of claim 18, wherein the polymeric filler comprises microcrystalline cellulose.

22. The dosage form of claim 21, wherein the microcrystalline cellulose has a particle size of 50 microns to 200 microns.

23. The dosage form of claim 18, wherein the binder comprises methylcellulose.

24. The dosage form of claim 20, wherein the ethyl cellulose and the polyvinyl pyrrolidone in the delayed release coating are in a weight ratio of approximately 2.3:1.

25. The dosage form of claim 1, comprising a tablet with at least two discrete segments, at least one of which contains the immediate release phentermine formulation and at least another of which contains the controlled release topiramate formulation.

26. The dosage form of claim 1, wherein the controlled release topiramate formulation comprises beads comprising topiramate dispersed within a delayed release matrix comprising methylcellulose, microcrystalline cellulose, ethylcellulose and polyvinyl pyrrolidine.

27. The dosage form of claim 1, wherein the controlled release topiramate formulation comprises beads comprising topiramate dispersed within a delayed release matrix comprising hydroxypropyl methyl cellulose.

28. The dosage form of claim 1, wherein the controlled release topiramate formulation comprises beads comprising topiramate dispersed within a delayed release matrix and comprising a polymer selected from methylcellulose, hydroxypropyl methylcellulose, hydroxypropyl cellulose, cellulose acetate, methacrylic acid copolymer and ethylcellulose.

29. The dosage form of claim 1, wherein the controlled release topiramate formulation comprises a topiramate dosage form coated by a gradually hydrolysable material.

30. The dosage form of claim 29 wherein the gradually hydrolysable material comprises one or more of ethylcellulose, povidone, microcrystalline cellulose and hydroxypropyl methylcellulose.

31. The dosage form of claim 1, wherein the controlled release topiramate formulation comprises a core comprising topiramate, microcrystalline cellulose and methylcellulose and wherein the core is coated with ethyl cellulose and povidone.

32. The dosage form of claim 8, wherein the unit dosage of phentermine is 3.75 mg and the unit dosage of topiramate is 23 mg.

33. The dosage form of claim 8, wherein the unit dosage of phentermine is 7.5 mg and the unit dosage of topiramate is 46 mg.

34. The dosage form of claim 8, wherein the controlled release topiramate formulation reaches a maximum plasma concentration at about 8 hours to about 10 hours (Tmax) after administration.

35. The dosage form of claim 8, wherein the controlled release topiramate formulation comprises beads comprising a core comprising topiramate dispersed in a gradually hydrolysable material comprising a binder, and a polymeric filler, and wherein the core is provided with a delayed release coating.

36. The dosage form of claim 8, wherein the controlled release topiramate formulation comprises a core comprising topiramate, microcrystalline cellulose and methylcellulose and wherein the core is coated with ethyl cellulose and povidone.

37. A packaged pharmaceutical preparation comprising a plurality of the unit dosage forms of claim 1 in a sealed container and instructions for administering the dosage forms orally to effect weight loss.

38. A packaged pharmaceutical preparation, comprising a plurality of the unit dosage forms of claim 1 each in a discrete sealed housing, and instructions for administering the dosage forms orally to effect weight loss.

* * * * *

UNITED STATES PATENT AND TRADEMARK OFFICE

CERTIFICATE OF CORRECTION

PATENT NO. : 9,011,905 B2
APPLICATION NO. : 14/495246
DATED : April 21, 2015
INVENTOR(S) : Thomas Najarian, Peter Y. Tam and Leland Wilson It is certified that error appears in the above-identified patent and that said Letters Patent is hereby corrected as shown below:

On the Title Page, Item (63) Related U.S. Application Data

Please replace "2009" with --2008--

In the Specification

At column 5 line 9 "4.92" should be "4.67"
At column 8 line 59 "4.92" should be "4.67"
At column 8 line 60 "195.69" should be "185.69"
At column 9 line 22 "4.92" should be "4.67"
At column 9 line 24 "9.84" should be "9.33"
At column 19 line 18 "4.92" should be "4.67"

In the Claims

At column 21 line 57 "4.92" should be "4.67" [claim 10]
At column 21 line 58 "4.92" should be "4.67" [claim 10]
At column 21 line 65 "9.84" should be "9.33" [claim 12]
At column 21 line 66 "9.84" should be "9.33" [claim 12]
At column 22 lines 17-18 "and the controlled" should be "and controlled" [claim 17]
At column 23 line 1 "29 wherein" should be "29, wherein" [claim 30]
At column 24 line 16 "preparation, comprising" should be "preparation comprising" [claim 38]
At column 24 line 18 "housing, and" should be "housing and" [claim 38]

Signed and Sealed this
Twenty-first Day of July, 2015

Michelle K. Lee

Michelle K. Lee
*Director of the United States Patent and Trademark Office*